(12) United States Patent
Gerlach et al.

(10) Patent No.: US 7,639,372 B2
(45) Date of Patent: Dec. 29, 2009

(54) SCANNING SYSTEM WITH STEREO CAMERA SET

(76) Inventors: Dieter Gerlach, 1450 E. South Street, Owosso, MI (US) 48867; Helmut Kellner, Mahneberg 18, Gleichen (DE) 37130

( * ) Notice: Subject to any disclaimer, the term of this patent is extended or adjusted under 35 U.S.C. 154(b) by 645 days.

(21) Appl. No.: 10/548,055

(22) PCT Filed: Mar. 8, 2004

(86) PCT No.: PCT/US2004/007088

§ 371 (c)(1),
(2), (4) Date: Sep. 2, 2005

(87) PCT Pub. No.: WO2004/081488

PCT Pub. Date: Sep. 23, 2004

(65) Prior Publication Data

US 2006/0182308 A1 Aug. 17, 2006

Related U.S. Application Data

(60) Provisional application No. 60/452,826, filed on Mar. 7, 2003, provisional application No. 60/475,153, filed on Jun. 2, 2003, provisional application No. 60/509,933, filed on Oct. 9, 2003.

(51) Int. Cl.
*G01B 11/24* (2006.01)
(52) U.S. Cl. ........................ 356/610; 345/644
(58) Field of Classification Search ........ None
See application file for complete search history.

(56) References Cited

U.S. PATENT DOCUMENTS 4,842,411 A 6/1989 Wood (Continued)

OTHER PUBLICATIONS

Roger Y. Tsai, "A Versatile Camera Calibration Technique for High-Accuracy 3D Machine Vision Metrology Using Off-the-Shelf TV Cameras and Lenses", IEEE Journal of Robotics and Automation, vol. RA-3, No. 4, Aug. 1987.

*Primary Examiner*—Gregory J Toatley, Jr.
*Assistant Examiner*—Rebecca C Slomski
(74) *Attorney, Agent, or Firm*—Peter J. Rashid

(57) ABSTRACT

A scanning system includes one or more stereo camera sets (10) for detecting qualitative and quantitative anomalies of an object (40). Each stereo camera set (10) includes two cameras (12, 14) and a projector (16). Each camera (12, 14) is calibrated to correct any distortion due to misalignment of the CCD matrix array (18) and deficiencies of the optical system. The projector (16) projects an absolute encoded pattern (32, 34, 36) onto the object (40) to be measured and is capable of varying the intensity of the emitted electromagnetic energy in the infrared, visible and ultraviolet spectrums. A plurality of camera sets (10) can be combined in a scanning system matrix (42, 44) capable of detecting anomalies of the object (40) in a three-dimensional room (26). The three-dimensional room (26) can be of any desirable size, depending on the number of stereo camera sets (10). The data from the cameras (12, 14) is pre-processed by gate arrays (62) before being transmitted via digital signal processors (66) to a computer interface (64) for display of the measurement. As a result, the amount of data transferred is streamlined, thereby reducing operating time and enabling the scanning system to very accurately detect anomalies of the object (40) in a very short period of time.

12 Claims, 6 Drawing Sheets

U.S. PATENT DOCUMENTS

| | | | |
|---|---|---|---|
| 5,608,529 A * | 3/1997 | Hori | 356/609 |
| 5,768,443 A | 6/1998 | Michael et al. | |
| 5,812,269 A | 9/1998 | Svetkoff et al. | |
| 6,081,273 A * | 6/2000 | Weng et al. | 345/420 |
| 6,219,442 B1 | 4/2001 | Harper et al. | |
| 6,937,348 B2 * | 8/2005 | Geng | 356/603 |
| 2002/0035455 A1 * | 3/2002 | Niu et al. | 703/4 |
| 2003/0164952 A1 * | 9/2003 | Deichmann et al. | 356/603 |

* cited by examiner

SCANNING SYSTEM WITH STEREO CAMERA SET

BACKGROUND OF THE INVENTION

1. Field of the Invention

This invention relates in general to surface inspection systems, and in particular, to a high speed scanning system for detecting anomalies of an object with high precision by using one or more stereo camera sets.

2. Description of the Related Art

Even the human eye with its remarkable ability to capture huge amounts of optical information cannot make measurements with precision and accuracy sufficient for quality control of parts requiring highly precise tolerances. Failure to achieve proper measurements can result in a wide range of problems. For example, failure to maintain dimensional tolerances for parts in an automobile engine may result in problems ranging from decreased system life to increase probability of failure under out of the ordinary conditions. Even where later system testing at a manufacturing facility can detect problems resulting from failure to meet dimensional tolerances, unacceptably high rejection rates on account of defective systems can result.

Moreover, even when human eye is capable of performing a required inspection, such factors as fatigue, lighting, distraction and so forth make human inspection unreliable.

Today, in an attempt to minimize those applications where human optical inspection is employed, to avoid the sometimes unpredictable problems caused by fatigue, distraction and other factors, industry has turned increasingly toward the implementation of computerized inspection systems. With such systems, however, the resolution of the optical inspection apparatus is far below that of the human eye.

Currently, many electronic imaging cameras use two dimensional arrays of light sensitive elements, sometimes of the type known as charged coupled devices (CCD) as photodetectors. The purpose of these devices is to convert an optical image into a video image. There are many relatively low priced color and black and white array CCD detectors available for video imaging, but they produce low quality images, as alluded to above. More particularly, CCD detectors and other video imaging devices suffer from a relatively low pixel count. For example, CCD photodetector arrays have the ability to produce quality images with a resolution of approximately 2048 by 2048 pixels. However, these arrays are presently very expensive. Moreover, these very large arrays tend to have defects such as inoperative pixels, inoperative clusters of pixels, or inoperative lines of pixels. When very high quality images are required this type of electronic imaging system is not only very expensive. Such systems may not even be capable of performing a high-quality, high precision measurement.

Linear photodetectors cost much less than array detectors because they have far fewer pixels and thus have correspondingly much higher manufacturing yields. Linear photodetectors, obviously, however, are capable of imaging only one line of information in an image that any given point in time using the single line of photo sensitive devices which they have. Accordingly, the linear photodetector must therefore scan the entire image, line by line.

The same is achieved by using a mechanical scanning assembly for moving the linear photodetector across the image plane in the camera. Generally, systems of this type derived image data by 1) relying upon the precision of the steady state operation of the mechanical scanning assembly, 2) assuming identical transient translational movements during the initiation of a scan, and 3) assuming that translational movement is uniform over time. Such a system, while suitable for making high quality digital images for commercial photography, is inappropriate for use in making high precision measurements.

More particularly, mechanical irregularities in the scanning assembly make the generation of highly precise image information impossible, thus making the image data captured by such systems on suitable for the purpose of confirming dimensional tolerances in a precision manufacturing environment.

Accordingly, it would be advantageous to have a device that will capture a single image of a part with enough precision that accurate measurements can be made of the features of such a part.

SUMMARY OF THE INVENTION

In one embodiment of the invention, a scanning system comprises a stereo camera set including a pair of cameras and a projector. Each camera has a CCD matrix array and an optical system corrected for distortion based on a dot matrix reference system. The projector includes a glass slide with an engraved absolute encoded pattern and a variable light source. The scanning system detects anomalies on a surface of an object when the object is placed within a three-dimensional room.

In another embodiment of the invention, a method of processing data in a scanning system comprises the steps of:

processing an array of data from scanning a surface of an object with a stereo camera set by using a hierarchical arrangement in which a gate array connected to a camera of the stereo camera set determines which data from the array of data is necessary for recognition of the object, and which data from the array of data is necessary for computer interface operation;

transmitting only data from the array of data which is necessary for computer Interface operation via a digital signal processor to a computer; and displaying the data which is necessary for computer interface operation on the computer.

DESCRIPTION OF THE PREFERRED EMBODIMENTS

Figure 1:
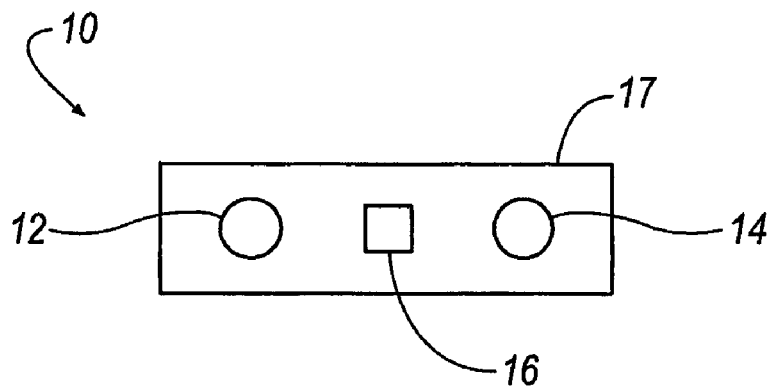
FIG. 1 shows a plan view of a scanning system comprising a stereo camera set according to an embodiment of the invention.

Referring now to FIG. 1, a scanning system according to the invention comprises a stereo camera set, shown generally at 10, that includes a pair of optical devices, such as cameras 12, 14 and an illumination device 16, such as a projector, or the like. The cameras 12, 14 and the projector 16 of the stereo camera set 10 may be mounted or affixed to a frame 17. The cameras 12, 14 are preferably cameras having a matrix array of charge-coupled devices (CCD) of a type well-known in the art. In addition, the invention is not limited by the type of camera, and the invention can be practiced with any desirable type of camera, such as a camera using Complementary Metal Oxide Semiconductor (CMOS) technology, or the like.

Figure 2:
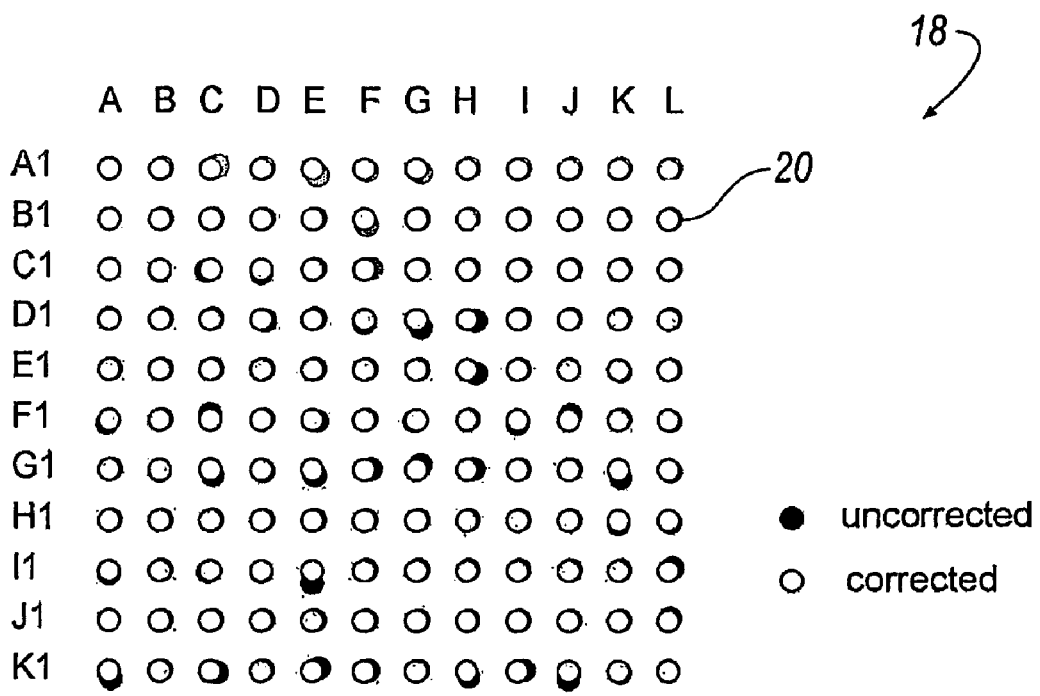
FIG. 2 shows a two-dimensional dot matrix array of a camera used in the stereo camera set having a CCD matrix illustrating uncorrected matrix dots and corrected matrix dots after the calibration process.

An ideal camera using a CCD matrix array, for example, has a distortion free optical system (e.g., a lens) and a perfectly arranged CCD matrix array that would "see" or detect a dot matrix reference system 18 of matrix dots 20, as shown by the white dots in FIG. 2. In reality, however, the camera 12, 14 includes some distortions in an optical system 15 and deficiencies in the arrangement of the CCD matrix array, and therefore detects a distorted position of the matrix dots 20, as shown by the dark dots in FIG. 2. The amount of distortion detected by each camera 12, 14 is dependent upon the severity of imperfections in the optical system 15 and deficiency of the CCD matrix array.

One aspect of the invention is a method to correct for deficiencies and distortions of optical systems in each camera 12, 14 by calibrating each camera 12, 14 of the optical system 15 using a calibration procedure to correct any distortion in the optical system and deficiencies in the arrangement of the CCD matrix array in each camera 12, 14. As a result of the calibration procedure, the scanning system of the invention can use any desirable relatively inexpensive calibrated camera, rather than an expensive high-resolution CCD matrix camera that may still include some distortions.

Figure 3:
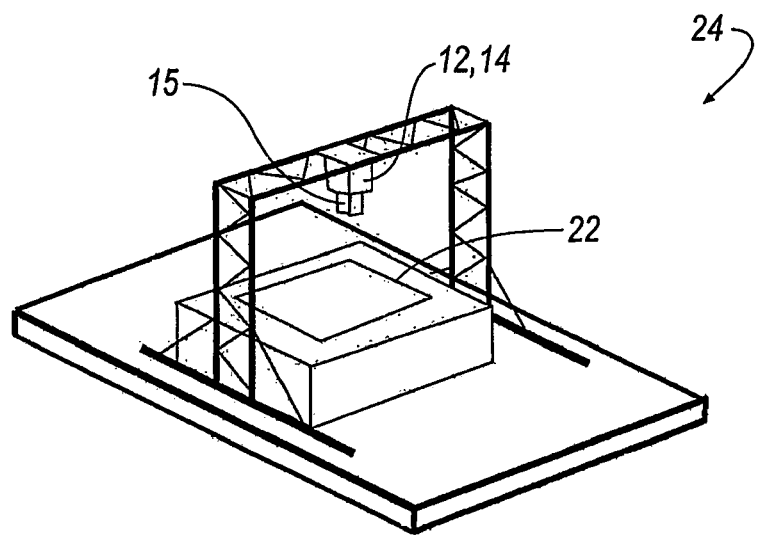
FIG. 3 shows a perspective view of calibration equipment used to calibrate each camera of the stereo camera set of the invention.

Referring now to FIG. 3, calibration of each camera 12, 14 is achieved by measuring the position of each dot 20 of the dot matrix reference system 18 within a field of view 22 of each camera 12, 14 on a very accurate coordinate positioning machine 24. Particularly, the position of each dot 20 of the dot matrix reference system 18 has its measured coordinate. The measured coordinate for the position of each dot 20 of the dot matrix reference system 18 is then used in a three-dimensional room, as described below. For each measurement, the distortion of the camera 12, 14 is completely corrected mathematically by using triangulation and statistical formulas that are well-known in the art.

By using the above calibration procedure, each pixel of the CCD matrix array of each camera 12, 14 is corrected for alignment errors and deficiencies in the optical system 15. As a result, the invention is not limited by the type of camera, and that the invention can be practiced by using any desirable camera regardless of the amount of resolution of the camera. Of course, cameras with higher resolution may be used and will result in less correction of the camera by the calibration process described above. Each camera used with the scanning system of the invention are consequently corrected and calibrated using the same calibration procedure.

Figure 4:
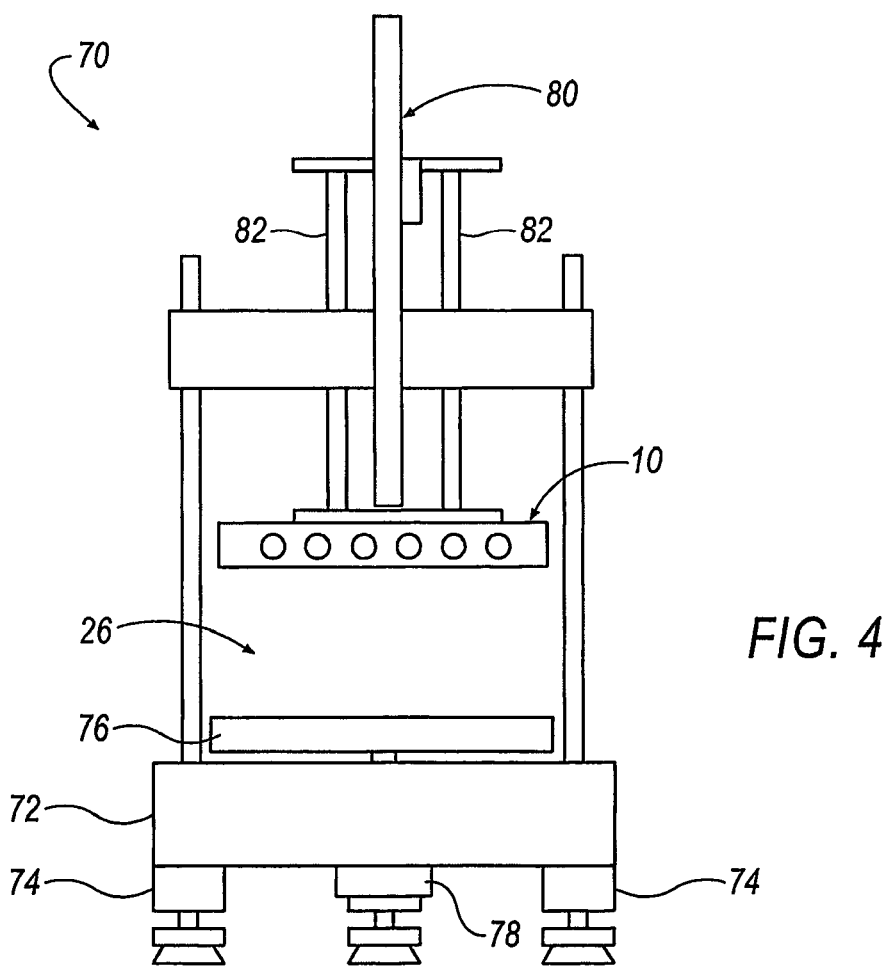
FIG. 4 shows an elevational view of calibration equipment used to calibrate the stereo camera set defining a three-dimensional room of the invention.
Figure 5:
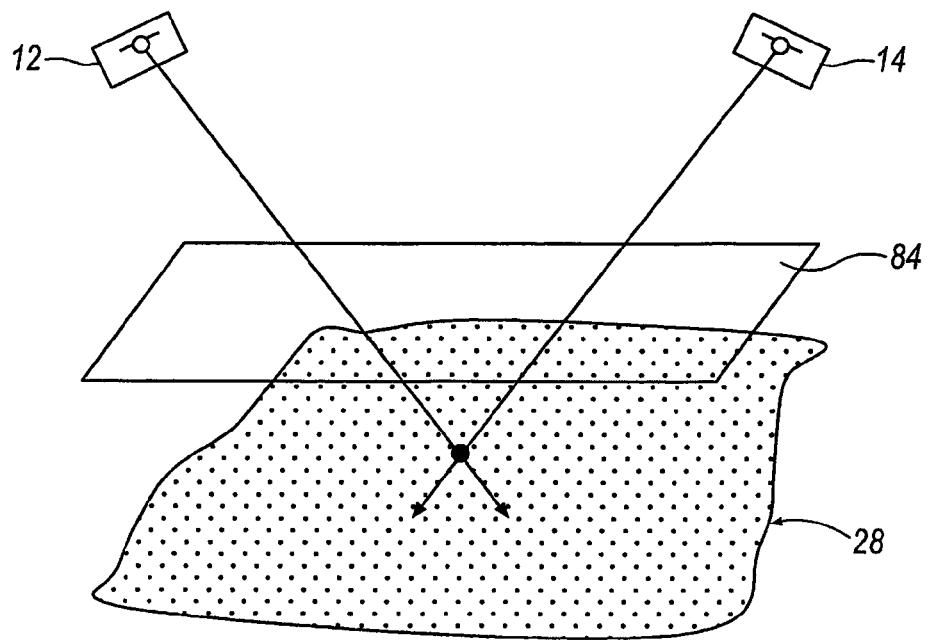
FIG. 5 shows a plan view of the triangulation method during calibration of the stereo camera set of the invention using the calibration equipment of FIG. 4.
Figure 6:
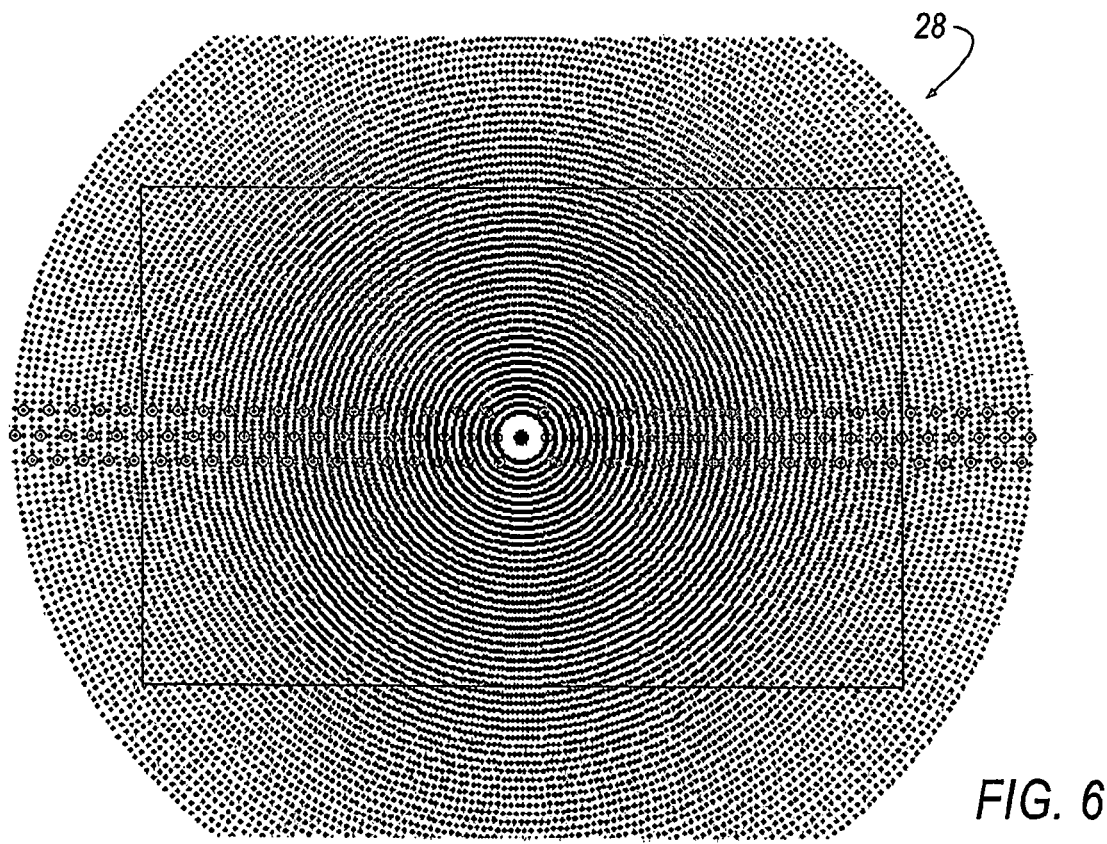
FIG. 6 shows a plan view of a reference pattern that is rotated in a complete circle at each selected elevation during calibration of the stereo camera set of the invention.

Referring now to FIGS. 4 and 5, once each camera 12, 14 is calibrated for alignment errors and deficiencies of the CCD matrix array in each camera 12, 14 of the optical system 15, the stereo camera set 10 with cameras 12, 14 (stereo cameras) is oriented towards each other and calibrated within a three-dimensional room 26. The calibration equipment, shown generally at 70, includes a platform 72 mounted on alignment pads 74. A code plate 76 is rotatably coupled to a rotary encoder 78 that is capable of accurately rotating the code plate 76 in a complete circle. The code plate 76 includes a reference pattern 28, for example, the reference pattern 28 as shown in FIG. 6. The calibration equipment 70 also includes a linear encoder 80 that is capable of accurate linear movement of the stereo camera set 10 in a z-direction or vertical direction. One or more guide members 82 may be included to assist in accurate linear movement of the stereo camera set 10 in the z-direction.

A calibration measurement is taken by the stereo camera set 10 by detecting the reference pattern 28 at a selected elevation in the z-direction. The projective interactions within the stereo camera set 10 are calculated with the use of triangulation functions that are well-known in the art to determine a virtual reference plane 84, as shown in FIG. 5. The results are further narrowed and evaluated by means of statistical methods that are well-known in the art. The statistical methods have the effect of large data reductions, which greatly decrease the amount of time needed to perform the measurement of the object 40, and thus increase the measurement speed.

After each calibration measurement, the reference pattern 28 is rotated at a predetermined increment, for example, 5 degrees, 10 degrees, or the like, and another calibration measurement is taken. This process is repeated until the reference pattern 28 is rotated a full 360 degrees. Then, the stereo camera set 10 is moved a predetermined amount in the z-direction, for example, 5 mm, 10 mm, 20 mm or the like, and the calibration process is repeated at the new selected elevation. The calibration is completed once the cameras 12, 14 are moved in the z-direction a predetermined distance, for example, 700 mm, or the like. The area defined by the field of view of the camera in the x- and y-directions, for example, 300 mm by 450 mm, and the distance in which the camera is moved in the z-direction, for example, 700 mm, defines the volume of a three-dimensional room 26. Because the calibration process can be performed for any desired dimensions of the three-dimensional room 26, the invention is not limited by size of the three-dimensional room 26, but can be of any desirable size depending on the dimensions of the calibration in the x-, y- and z-directions.

Once all the measurements are taken, the data from the measurements are arranged in the form of look up tables in which data of mechanical and temperature influences are taken into account to guarantee the overall accuracy of the stereo camera set 10. The use of look up tables also ensures that error propagation, systematic, and non-systematic errors will be avoided throughout the entire scanning measurement. After calibration of the stereo camera set 10, the stereo camera set 10 was verified to have an accuracy of greater than 40μ. The accuracy may be increased much higher with the use of cameras with larger CCD matrix arrays in conjunction with improved optics (lenses).

Figure 7:
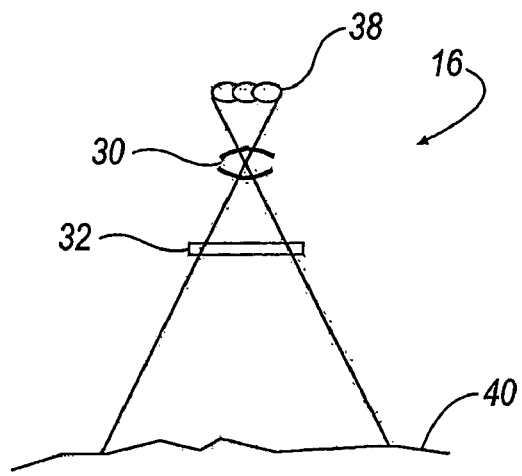
FIG. 7 shows a schematic view of a projector used in the stereo camera set of the invention.
Figure 8:
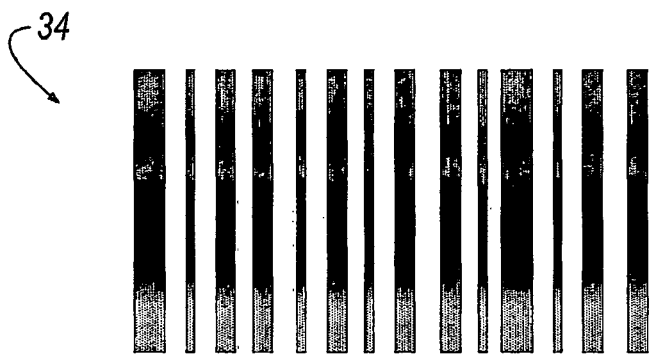
FIG. 8 shows a plan view of an absolute encoded stripe pattern that is projected onto the surface of the object to be measured by the projector in accordance with the principles of the invention.
Figure 9:
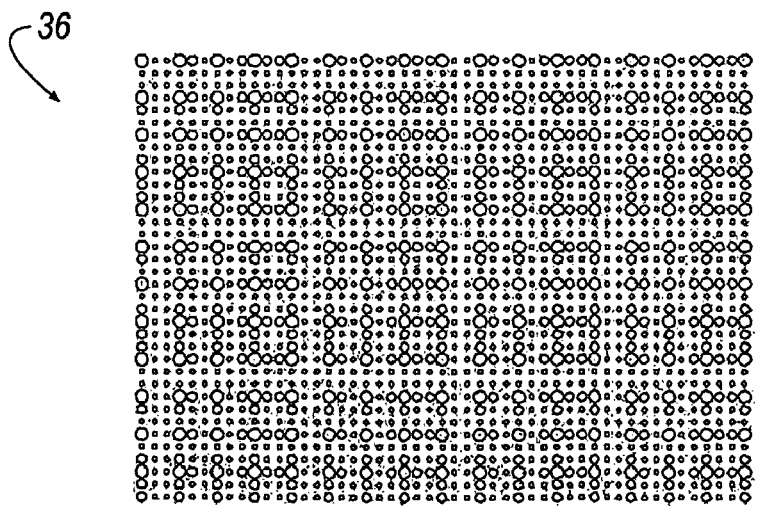
FIG. 9 shows a plan view of an absolute encoded round pattern that is projected onto the surface of the object to be measured by the projector in accordance with the principles of the invention.

Referring now to FIG. 7, the projector 16 used in the stereo camera set 10 comprises an optical system 30 (i.e., lens, or the like) and an absolute encoded pattern 32 engraved on, for example, a glass slide. One absolute encoded pattern 32 may comprise, for example, a stripe pattern 34 as shown in FIG. 8. An alternate absolute encoded pattern 32 may comprise, for example, a round pattern 36 as shown in FIG. 9. It will be appreciated that other absolute encoded patterns are contemplated by the invention. The round pattern 36 may be more desirable than the stripe pattern 34 because only one camera set 10 is needed to perform a three-dimensional measurement, rather than two camera sets 10 (one stereo camera set 10 projecting the stripe pattern 34 in the x-direction and another stereo camera set 10 projecting the stripe pattern 34 in the y-direction) is needed when using the stripe pattern 34.

Referring back to FIG. 7, the projector 16 also includes a light source 38 capable of emitting electromagnetic energy in the infrared, visible or ultraviolet frequencies. The intensity of the electromagnetic energy can be varied by the light source. The spectrum (infrared, visible or ultraviolet) in which the electromagnetic energy is emitted depends on the surface characteristics of the object to be measured. It is envisioned that other frequencies of electromagnetic energy, such as x-ray, are also contemplated by the invention.

The purpose of the light source 38 is to project the absolute encoded pattern 32 onto any given surface of an object 40 to be measured to provide a detectable optical reference structure on the surface of the object 40. Projecting the absolute encoded pattern 32 enables mathematical measurements of the anomalies on the surface of the object 40, such as a "qualitative" condition and/or a "quantitative" condition of the surface of the object 40. The qualitative condition of the object 40 includes, for example, dents, surface imperfections, deformation, or the like. The quantitative condition of the object 40 includes, for example, the relative elevation between two portions of the object (flush), gap, diameter of holes, or the like.

Before the stereo camera set 10 will scan and measure an anomaly on the surface of the object 40, the surface characteristics of the object 40 are detected and used to adjust for a suitable illumination in direct conjunction with the surface characteristics of the object 40. For example, the frequency of the light source can be changed, depending on the optical characteristics of the surface of the object 40, such as color, reflectivity, or the like. Because reflective surfaces, such as chrome, polished metal, or the like, and different colors, such as black, red, or the like, are difficult to scan, the projector 16 is capable of emitting electromagnetic energy at a selected frequency, depending on the surface condition of the object 40. For example, the projector 16 is capable of emitting electromagnetic energy at a different frequency for a red colored surface than for a gray colored surface, or a highly reflective surface. By emitting electromagnetic energy a selected frequencies, unwanted results, such as reflections, overexposure and/or other light-surface measurement related problems, are avoided. Together with the use of light frequencies, polarization filters (not shown) can be used depending on the reflective ness of the object to be measured.

For example, the light source 38 can comprise of three (or more) basic light sources in the color of green, blue and red. Based on the detected surface color and circumstances, e.g. reflective ness, the frequency of the color of emitted light can be adjusted and/or mixed using the base colors of green, blue and red being mixed towards an object fitting illumination. The entire light frequency band will be utilized and used which includes ultra violet light as well.

The frequency of the light source 38 can be changed with the use of color filters (not shown). In addition, the intensity of the electromagnetic energy emitted from the light source 38 and the timing of the electromagnetic energy emitted from the light source 38 can be varied. For example, the light source 38 can emit electromagnetic energy at predetermined time intervals, such as in a strobe light, or the like. To perform three-dimensional measurements with the stereo camera set 10, it may be necessary to move the absolute encoded pattern 32 in the x- and y-directions. Because the pattern 32 is absolutely encoded, the movement of the absolute encoded pattern 32 should be achieved using an accurate mechanical control mechanism, such as a step motor and cams, or the like.

The stereo camera set 10 comprising the pair of cameras 12, 14 and the projector 16 cover the field of view 26 and is used to scan the surface of the object 40 as large as the field of view 26 has been established. Because of the cameras 12, 14 have been previously calibrated to correct any distortions, and because the projector 16 has special features, the stereo camera set 10 is capable of measuring the qualitative and quantitative surface conditions of the object 40 very accurately to a factor greater than ±50 micro mm. Tests have confirmed that the round absolute encoded pattern 38 enhances the overall accuracy, as compared to the stripe pattern 36. The use of CMOS cameras, rather than CCD cameras, increase the accuracy of the stereo camera set to around ±5 micro mm.

Figure 10:
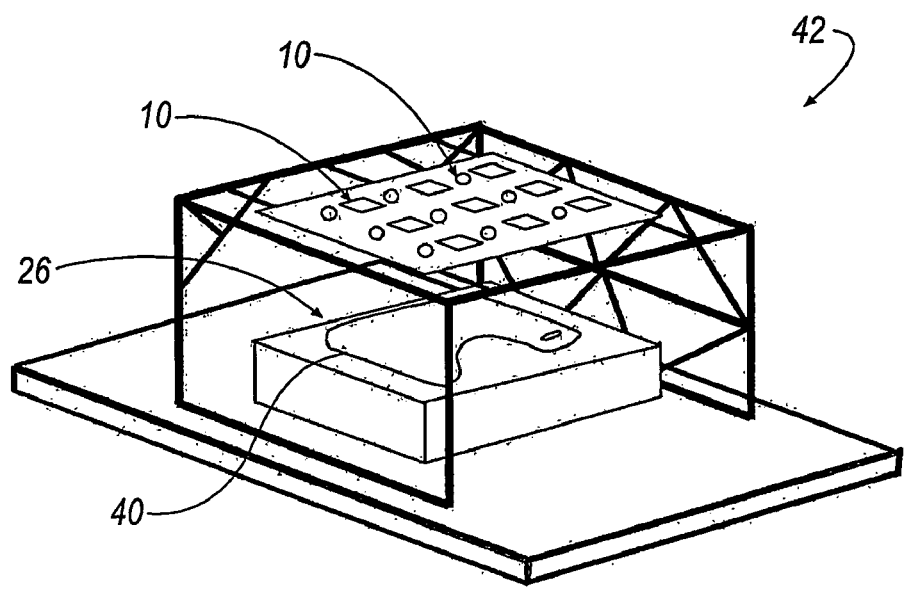
FIG. 10 shows a perspective view of a fixed scanning matrix system with a plurality of stereo camera sets according to an embodiment of the invention.

In one aspect of the invention, the scanning system can comprise a plurality of stereo camera sets 10, for example, nine stereo camera sets 10, to form a fixed scanning matrix 42 that enables scanning of large surfaces in the three-dimensional room 26, as shown in FIG. 10. Thus, the individual stereo camera sets 10 are aligned in different arrangement in order to satisfy the results of the object 40 to be measured. The scanning matrix 42 may comprise an unlimited number of individual stereo camera sets 10 and is only limited by the size of the object to be measured.

Figure 11:
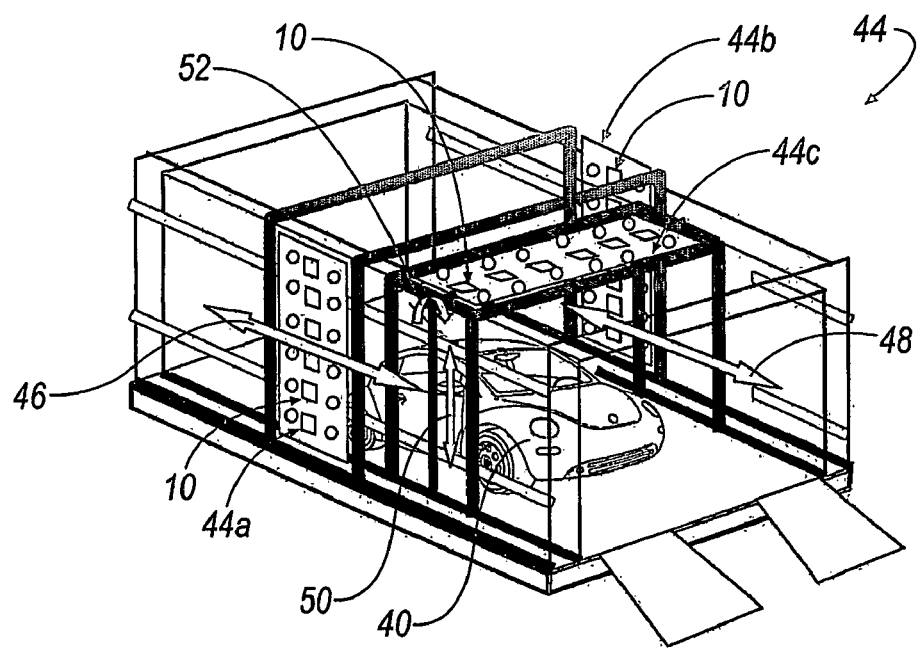
FIG. 11 shows a perspective view of a movable scanning matrix system with a plurality of stereo camera sets according to an embodiment of the invention.

In another embodiment of the invention, the scanning system can include a plurality of stereo camera sets 10 to form a movable scanning matrix 44 that enables the detection of anomalies of the object 40, such as a motor vehicle, as shown in FIG. 11. In the illustrated embodiment, the movable scanning matrix 44 includes three separate scanning matrices 44*a*, 44*b*, 44*c*. The scanning matrices 44*a*, 44*b* are capable of linear reciprocating movement in the horizontal direction on each side of the object 40, as indicated by the arrows 46, 48, respectively. The scanning matrix 44*c* is capable of linear reciprocating movement in the vertical direction (z-direction), as indicated by the arrow 50, and rotating movement, as indicated by the arrow 52.

Figure 12:
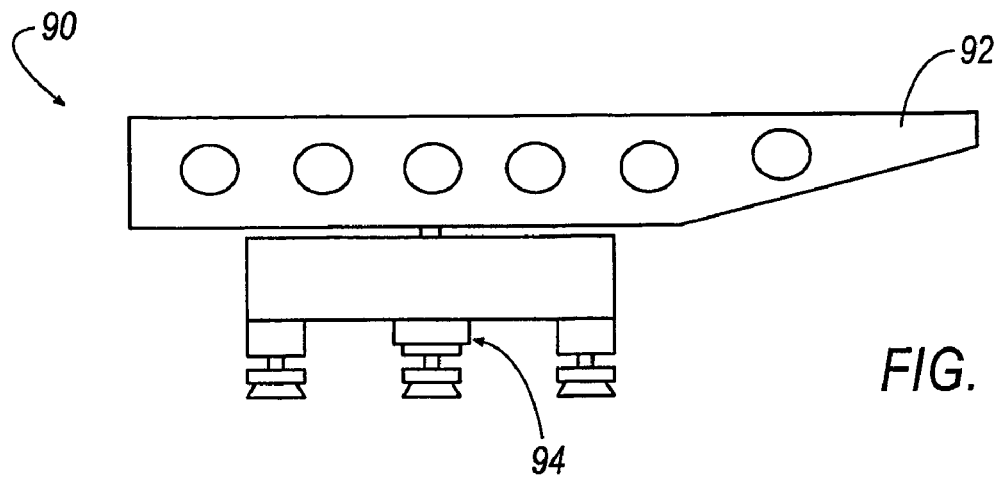
FIG. 12 shows an elevation view of calibration equipment used to calibrate the scanning matrix system according to the invention.

After calibrating each stereo camera set 10 as described above, the scanning matrix 42, 44 of more than one stereo camera sets 10 is calibrated combining all participating single stereo camera sets 10 in the matrix 42, 44, as shown in FIG. 12. For example, a calibration unit 90 for 24 stereo camera sets 10 can be combined to form a scanning matrix of approximately 1500 mm by 1500 mm. The calibration is performed similar to the single stereo camera set 10, as described above in FIGS. 4-6. The calibration is using again a rotary code plate 92 having a length of approximately 1000 mm, which rotates 360° using a rotary encoder 94, but has no movement into the z-direction to cover the 1500 mm×1500 mm×700 mm scanning area.

When performing a scanning measurement, the amount of data that has to be computed in using the presently available technology (e.g. frame grabber) has a very significant high impact on necessary computing power. Thus, the amount of large parallel processing using picture recognition through conventional scanning systems is extremely time consuming.

Figure 13:
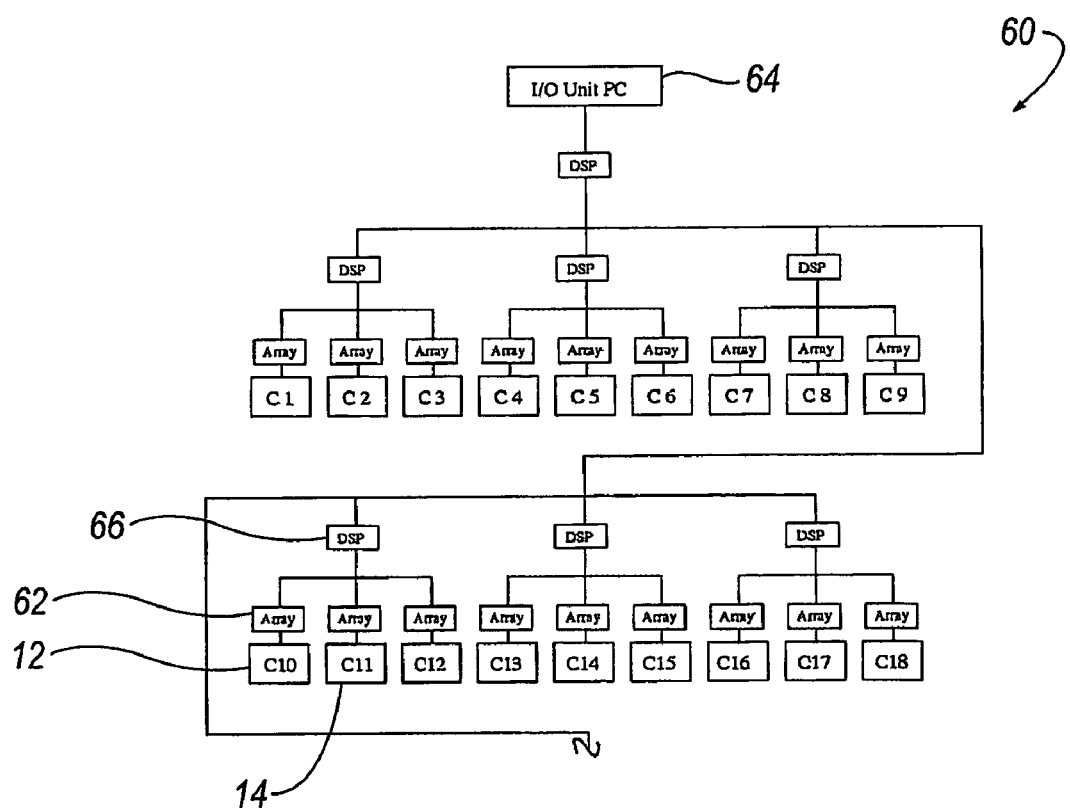
FIG. 13 shows a block diagram of a hierarchical arrangement for processing data from each camera of the stereo camera sets of the invention.

Referring now to FIG. 13, to connect any number of cameras 12, 14 of the scanning matrix 42, 44 efficiently as far as speed and processing data are concerned; a hierarchic arrangement 60 for data processing and interfacing is realized by the invention. In the invention, the hierarchic arrangement 60 enables the processing of data from an unlimited amount of cameras (integrated stereo camera sets 10). The hierarchic arrangement 60 is based on the functional principle that ensures that all data that needs to be "crunched" or processed for object recognition for each camera 12, 14 is computed in gate arrays 62. The gate arrays 62 are programmed to ensure that only the results of the computation and the necessary amount of data required for interface operation with a personal computer 64 (PC) (i.e., displaying the object on a display screen) will be transferred to the input/output (I/O) interface of the PC 64 via digital signal processors (DSPs) 66. All other data, originally necessary for the computation of the object recognition by the cameras 12, 14 will be disregarded after completing the computation in the gate arrays 62. Hence, the disregarded data will not be transmitted to the I/O interface of the PC 64. As a result, a streamlining effect on the amount of data to be transferred is achieved, thereby reducing and minimizing the necessary computation requirements of the PC 64, thereby reducing operating time and enabling the scanning system to very accurately detect anomalies of the object 40 in a very short period of time. In addition, the streamlining effect on the amount data to be transferred reduces the overall operating time for measuring large surfaces of an object 40.

Because the programmed gate arrays pre-process the data, the DSPs 66 are for interface processing only. Rather, the purpose of the DSPs 66 is to act as a system bus and ensure that there are no timing problems during the transfer of data from the gate arrays 62 to the I/O of the PC 64. It will be appreciated that the amount of data can also be reduced by selecting a desired number of stereo camera sets 10 in one or more scanning matrices 44a, 44b, 44c, depending on the physical characteristics of the object 40. For example, if a small object is to be measured, the scanning system of the invention can select only a few stereo camera sets 10 for one or more scanning matrices 44a, 44b, 44c that will provide a sufficient amount of data to enable measurement of the object 40. On the other hand, if a larger object is to be measure, the scanning system can select a larger number of stereo camera sets 10 for measuring the object 40.

While the invention has been specifically described in connection with certain specific embodiments thereof, it is to be understood that this is by way of illustration and not of limitation, and the scope of the appended claims should be construed as broadly as the prior art will permit.

What is claimed is:

1. A scanning system for detecting an anomaly on a surface of an object (40) when the object is placed within a three-dimensional room (26), the system comprising:
   a calibrated stereo camera set (10) including a pair of cameras (12, 14), each camera (12, 14) being calibrated for distortion following a calibration process comprising measuring a position of each dot (20) of a dot matrix reference system (18) within a field of view (22) of each camera (12, 14), and calibrating the stereo camera set (10) by moving the dot matrix reference system (18) in two-dimensions while the stereo camera set (10) is located at a plurality of selected elevations, thereby defining the three-dimensional room (26); and
   a projector (16) having a medium with absolute encoded pattern (32) thereon, and a light source (38) for projecting the absolute encoded pattern (32) on the surface of the object (40).

2. The scanning system according to claim 1, further comprising a plurality of camera sets (10) arranged in a scanning matrix (42, 44) for scanning the surface of the object (40) in the three-dimensional room (26).

3. The scanning system according to claim 1, wherein the light source (38) of said projector (16) is capable of emitting electromagnetic energy at three different frequencies onto a surface of the object (40), the light source (38) capable of varying an intensity of each of the three frequencies of electromagnetic energy.

4. The scanning system according to claim 3, wherein a frequency of the light source is selected based on an optical characteristic of the surface of said object (40).

5. The scanning system according to claim 3, wherein the projector (16) emits the absolute encoded pattern (42, 44) in both a first direction and a second direction.

6. The scanning system according to claim 3, wherein the electromagnetic energy is in the form of visible light.

7. The scanning system according to claim 3, wherein the frequency and intensity of said electromagnetic energy varies as a function of time.

8. The scanning system according to claim 1, wherein the absolute encoded pattern (32) comprises a stripe pattern (34).

9. The scanning system according to claim 1, wherein the absolute encoded pattern (32) comprises a pattern (34) of round dots.

10. The scanning system according to claim 1, wherein the object (40) is recognized by the stereo camera set (10) by using a hierarchical arrangement (60) in which a gate array (62) determines which data from an array of data is necessary for recognition of the object (40), and which data is necessary for computer interface operation.

11. the scanning system according to claim 1, wherein the light source (38) varies and intensity of the electromagnetic energy emitted from the light source (38).

12. the scanning system according to claim 1, wherein a spectrum of electromagnetic energy emitted from the object (40) depends on a surface characteristic of the object (40).

* * * * *